(12) United States Patent
Matayoshi et al.

(10) Patent No.: US 10,269,117 B1
(45) Date of Patent: Apr. 23, 2019

(54) SYSTEMS AND METHODS FOR MORPHOLOGY ANALYSIS

(71) Applicant: ABBVIE INC., North Chicago, IL (US)

(72) Inventors: Edmund Matayoshi, Richmond, IL (US); Jie Wang, Bluff, IL (US); Sheng Tu, Libertyville, IL (US)

(73) Assignee: ABBVIE INC., North Chicago, IL (US)

( * ) Notice: Subject to any disclaimer, the term of this patent is extended or adjusted under 35 U.S.C. 154(b) by 11 days.

(21) Appl. No.: 15/478,841

(22) Filed: Apr. 4, 2017

Related U.S. Application Data

(60) Provisional application No. 62/318,021, filed on Apr. 4, 2016.

(51) Int. Cl.
*G06K 9/00* (2006.01)
*G06T 7/00* (2017.01)

(52) U.S. Cl.
CPC .. *G06T 7/0012* (2013.01); *G06T 2207/10056* (2013.01)

(58) Field of Classification Search
CPC ............... G06T 7/0012; G06T 7/0083; G06T 2207/30004; G06T 7/0081; G06T 2207/10116; G06T 5/40; G06T 2207/30068; G06F 19/321
See application file for complete search history.

(56) References Cited

U.S. PATENT DOCUMENTS

| 2016/0095980 A1* | 4/2016 | Denina ............... A61M 5/3129 356/241.1 |
| 2017/0056923 A1* | 3/2017 | Hioki ................. A61M 5/3129 |
| 2017/0108451 A1 | 4/2017 | Gertz et al. |
| 2017/0153431 A1 | 6/2017 | Nguyen et al. |

OTHER PUBLICATIONS

Dixit et al., "Effect of Processing Parameters on the Physical Stability of Silicone Coatings," AAPS PharmSciTech, 13(4):1116-1119 (2012).
http://www.siliconization.com/newsexhibitions/news.html (Accessed on Jul. 11, 2017).
http://www.zebrasci.com/ (Accessed on Jul. 11, 2017).
Ingle and Agarwal, "Pre-filled syringe—a ready-to-use drug delivery system: a review," Expert Opin. Drug Deliv., 11(9):1391-1399 (2014).

(Continued)

*Primary Examiner* — Duy M Dang
(74) *Attorney, Agent, or Firm* — Baker Botts L.L.P.

(57) ABSTRACT

Inspection of distribution and morphology of a substance applied to a container includes selectively illuminating at least a portion of a surface of a container using a light source, adjusting the light source to create a resolved view of the substance with sufficient contrast to show a layer of the lubricant disposed on the surface of the container, obtaining an image of the resolved view of the illuminated portion of the surface of the container using an image detector, analyzing image data representing the image of the resolved view, using a data processor, to generate a quantity representing a quality of interaction between the lubricant and the surface of the container, and determining whether the container is acceptable based upon the quantity generated.

20 Claims, 8 Drawing Sheets
(1 of 8 Drawing Sheet(s) Filed in Color)

(56) References Cited

OTHER PUBLICATIONS

Prefilled Syringes: Innovations That Meet the Growing Demand, 2005 http://www.ondrugdelivery.com/publications/prefilled_syringes.pdf.

Reuter and Petersen, "Syringe Siliconization: Trends, methods, analysis procedures," TechnoPharm 2(4):238-244 (2012).

Sacha et al., "Pre-filled syringes: a review of the history, manufacturing and challenges," Pharmaceutical Development and Technology, 20(1):1-11 (2015).

Wen et al., "Distribution of Silicone Oil in Prefilled Glass Syringes Probed with Optical and Spectroscopic Methods," PDA Journal of Pharmaceutical Science and Technology 63:149-158 (2009).

* cited by examiner

SYSTEMS AND METHODS FOR MORPHOLOGY ANALYSIS

CROSS-REFERENCE TO RELATED APPLICATION

This application claims the benefit of U.S. Provisional Application No. 62/318,021, filed Apr. 4, 2016, which is incorporated by reference herein in its entirety.

BACKGROUND

Field of the Disclosed Subject Matter

The present disclosed subject matter relates to systems and methods for inspecting distribution and morphology of a substance applied to a container, such as a lubricant applied to a syringe.

Description of Related Art

Prefilled syringes can be used for injectable drugs (including biologics). Glass based syringes are one type of prefilled syringe, and adequate lubrication of the inside surface can improve injection performance. Lubrication can also affect injection performance of auto-injectors, which can be ineffective when lubrication is inadequate. Silicone oil is one type of lubricant used to lubricate prefilled syringes. The amount of silicone oil as well as its distribution on the glass surface can affect the quality of lubrication.

Certain invasive or destructive techniques can be used to characterize silicone oil in prefilled syringes. Fourier Transform Infrared Spectroscopy (FTIR) and Inductively Coupled Plasma Spectroscopy (ICP) can be used to measure the total amount of silicone oil present in a syringe; both methods utilize a solvent to remove all silicone oil from the syringe surface, and neither provides suitable information on the distribution of silicone oil on the walls of the syringe. Glass dust test can be used to make silicone oil visible for visual inspection, and its spatial resolution can be limited. Gliding force measurement is an indirect inspection method, but can be destructive to the lubricant or syringe contents.

Certain noninvasive optical spectroscopic technologies can also be applied to evaluate the oil coating. One instrument that can be used to perform such techniques is the Layer Explorer, manufactured by RapID, which uses thin-film reflectometry to determine the amount as well as the distribution of silicone oil coating in syringes. The spatial resolution of such techniques can be limited to several hundreds of microns, which can be inadequate for differentiating ill-behaved syringes from well-behaved syringes. In addition, such techniques can apply exclusively to empty syringes, which can be ineffective to detect changes in the silicone oil layer in the presence of the formulated drug solution.

Another technique by ZebraSCI involves instruments based on Schlieren visualization methods for utilizing refractive index inhomogeneity presented by the oil layer. ZebraSCI instrumentation can image filled syringes to provide information on the distribution of silicone oil on the syringe surface. However, optical defects distorting the image can be misinterpreted as silicone oil variability on the surface. In addition, the information provided by ZebraSCI can be inadequate to detect certain ill-behaved syringes. Further techniques include confocal Raman microscopy and 3D laser scanning microscopy to evaluate silicone oil coating in empty syringes. However, these techniques can involve complex instrument systems and can be unsuitable for high-throughput inspection desirable in a pharmaceutical manufacturing environment.

The systems and techniques described above can be unsuitable to provide sufficient resolution for evaluating the morphology at the requisite level of detail and thus can fail to correlate with injection test results. As such, there remains a need for systems and methods that can assess silicone oil layer interaction strength that correlates with injection test performance, including systems and methods that can non-invasively provide high-throughput evaluation of suitability of container lubrication, particularly in pre-filled syringes.

SUMMARY

The purpose and advantages of the disclosed subject matter will be set forth in and apparent from the description that follows, as well as will be learned by practice of the disclosed subject matter. Additional advantages of the disclosed subject matter will be realized and attained by the methods and systems particularly pointed out in the written description and claims hereof, as well as from the drawings.

To achieve these and other advantages and in accordance with the purpose of the disclosed subject matter, as embodied and broadly described, the disclosed subject matter includes a method for inspecting a distribution and a morphology of a substance in a container. The method includes selectively illuminating at least a portion of a surface of a container using a light source; adjusting the light source to create a resolved view of the substance with sufficient contrast to show a layer of the lubricant disposed on the surface of the container; obtaining an image of the resolved view of the illuminated portion of the surface of the container using an image detector; analyzing image data representing the image of the resolved view, using a data processor, to generate a quantity representing a quality of interaction between the lubricant and the surface of the container; and determining whether the container is acceptable based upon the quantity generated.

For example and as embodied herein, the substance can include a silicone oil. Additionally or alternatively, the container can include a pre-filled syringe. The light source can include a point light source and/or collimated light.

Additionally, and as embodied herein, adjusting the light source includes adjusting at least one of an angle and a distance of the light source relative to the container to control the balance of contributions from bright field and dark field illumination of the sample to be collected by the detector, thereby creating the resolved view with sufficient contrast to show the layer of the substance disposed on the surface of the container. Additionally or alternatively, adjusting the light source can include modifying a size of a center beam blocker of a conventional dark field microscope. Adjusting the light source can further include selecting the size of the center beam blocker to allow a contribution from bright field imaging to create the resolved view with sufficient contrast to show the layer of the substance disposed on the surface of the container.

Furthermore and as embodied herein, the image detector can include a digital microscope. The digital microscope can have a resolution of about 20 microns or less.

In addition, and as embodied herein, analyzing the image data can include recognizing patterns and morphologies of illuminated regions of the substance. Analyzing the image data can further include comparing the recognized patterns and morphologies to a set of known image data, and each known image data of the set can have a known quantity representing a known quality of interaction between a sample substance and a sample container. Analyzing the image data can thus further include assigning a score to the container based on the comparison of the recognized patterns and morphologies to the set of known image data.

Additionally or alternatively, and as embodied herein, the method can further include obtaining a plurality of images of the resolved view of the illuminated portion of the surface of the container. The method can further include changing the focal distance of the image detector for each of the plurality of images of the resolved view. Analyzing the image data can thus include determining whether an area of illuminated regions of the lubricant has a substantially constant size or intensity in each of the plurality of images of the resolved view.

Additionally, and as embodied herein, the method can include further comprising identifying regions of strongly and weakly bound lubricant, and rejecting the container if the quantity is below a predetermined threshold. The detection can be performed on a plurality of containers in a high-throughput manner.

The disclosed subject matter also includes a system for inspecting a distribution and a morphology of a lubricant in a container. The system includes a light source configured to selectively illuminate at least a portion of a surface of a container. The light source is adapted to be adjusted to create a resolved view of the lubricant with sufficient contrast to show a layer of the lubricant disposed on the surface of the container. The system further includes an image detector configured to obtain an image of the resolved view of the illuminated portion of the surface of the container; and a data processor coupled to the image detector and configured to analyze image data representing the image of the resolved view to generate a quantity representing a quality of interaction between the substance and the surface of the container, and determine whether the container is acceptable based upon the quantity generated. The system can include any or all of the features described herein.

It is to be understood that both the foregoing general description and the following detailed description are exemplary and are intended to provide further explanation of the disclosed subject matter claimed.

The accompanying drawings, which are incorporated in and constitute part of this specification, are included to illustrate and provide a further understanding of the disclosed subject matter. Together with the description, the drawings serve to explain the principles of the disclosed subject matter.

BRIEF DESCRIPTION OF THE DRAWINGS

The application file contains at least one drawing executed in color. Copies of this patent with color drawings will be provided by the Office upon request and payment of the necessary fee.

DETAILED DESCRIPTION OF THE PREFERRED EMBODIMENT

Reference will now be made in detail to the various exemplary embodiments of the disclosed subject matter, exemplary embodiments of which are illustrated in the accompanying drawings. The structure and corresponding method of operation of the disclosed subject matter will be described in conjunction with the detailed description of the system.

The systems and methods described herein can be used to analyze a substance applied to any container. For purpose of illustration of the disclosed subject matter, and not limitation, reference is made herein to a substance applied to pre-filled syringes. It is understood, however, that the systems and methods described herein can be used to analyze a substance applied to any container, for example and without limitation, pre-filled devices, cartridges, or needle-free delivery systems, whether for medical use or for non-medical use. Additionally, for purpose of illustration of the disclosed subject matter, and not limitation, reference is made herein to silicone oil applied to a prefilled syringe. It is understood, however, that any substance can be analyzed in accordance with the disclosed subject matter, including but not limited to, mineral oils, vegetable oils, synthetic oils and dry lubricants.

For example, and as embodied herein, the systems and methods described herein can be used to analyze the interaction strength between silicone oil and the glass surface in a prefilled syringe. The interaction strength between lubricant and glass surface in a prefilled syringe can affect injection performance due at least in part to factors such as the composition of the formulation solution, the choice of siliconization procedure, the properties of the silicone oil, and the storage and handling procedures employed prior to filling the syringe with a drug product. The correlation between interaction strength and lubrication effectiveness can occur at least in part because if affinity is weak, the oil can have a propensity to form beads in the presence of an aqueous solution, which can contain a surfactant and a high concentration of protein. Weakly bound silicone oil beads can move away from the surface upon movement of the plunger during injection and thus can contribute poorly to lubrication. The interaction strength between the silicone oil coating and a glass surface in a filled syringe can be evaluated by high resolution imaging of the morphology of the silicone oil coating layer. The interaction strength between oil and surface can be ascertained at least in part because the morphology revealed at sufficient resolution and contrast can provide an indicator of surface contact angle.

In accordance with the disclosed subject matter herein, a method for inspecting a distribution of a substance in a container generally includes selectively illuminating at least a portion of a surface of a container using a light source; adjusting the light source to create a resolved view of the lubricant with sufficient contrast to show a layer of the lubricant disposed on the surface of the container; obtaining an image of the resolved view of the illuminated portion of the surface of the container using an image detector; analyzing image data representing the image of the resolved view, using a data processor, to generate a quantity representing a quality of interaction between the lubricant and the surface of the container; and determining whether the container is acceptable based upon the quantity generated.

The accompanying figures, where like reference numerals refer to identical or functionally similar elements throughout the separate views, further illustrate various embodiments and explain various principles and advantages all in accordance with the disclosed subject matter. For purpose of explanation and illustration, and not limitation, exemplary embodiments of systems and methods for inspecting a distribution of a lubricant in a container in accordance with the disclosed subject matter are shown and described below.

Figure 1A:
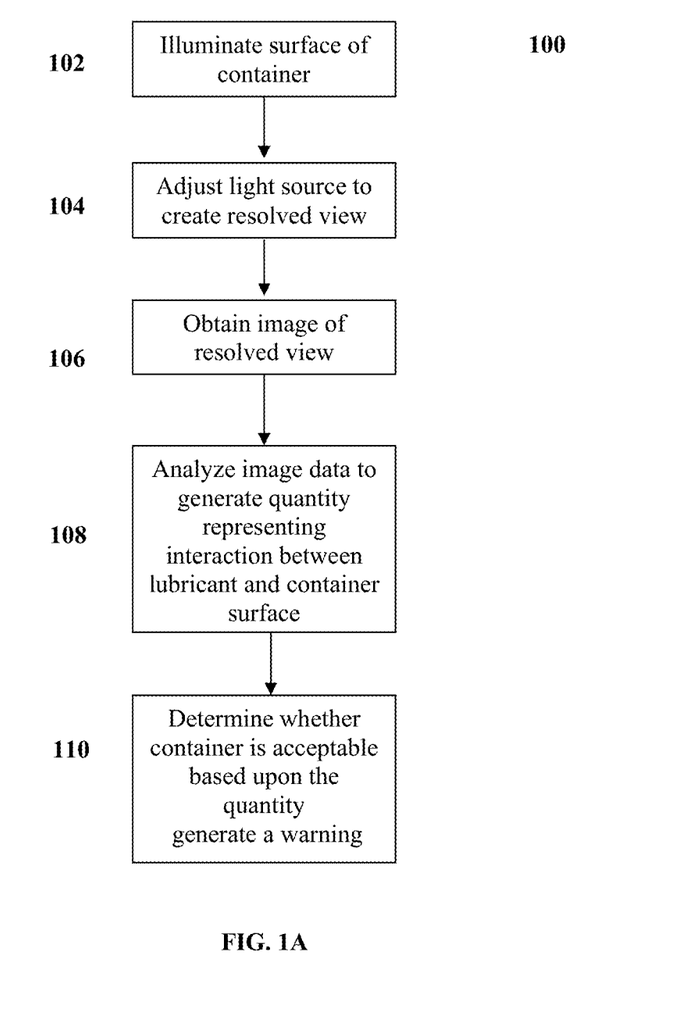
FIG. 1A is a diagram illustrating a representative method implemented according to an illustrative embodiment of the disclosed subject matter.
Figure 1B:
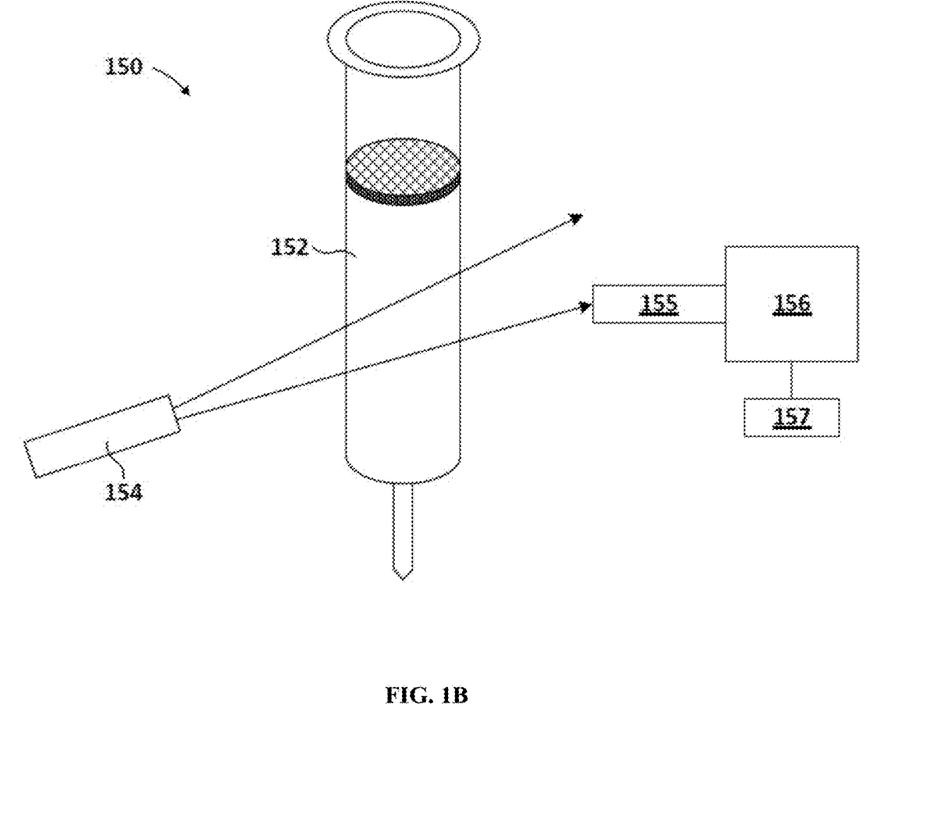
FIG. 1B is a diagram illustrating a representative system implemented according to an illustrative embodiment of the disclosed subject matter.

With reference to the exemplary method 100 of FIG. 1A in conjunction with the exemplary system 150 of FIG. 1B, the exemplary system includes a digital optical microscope and an illumination system. At 102, a surface of a container is illuminated by a light source which can be configured, for example and without limitation, as a point light source, a collimated light or any other suitable light source. For example, and as embodied herein, a point light source 154 is provided to illuminate a syringe 152. As embodied herein, the point light source 154 can be configured as a fiber coupled light source, but other light sources can be used, such as a rod or gas laser. At 104, the light source is adjusted, either manually or automatically, to create a resolved view for imaging. The resolved view can be produced, as embodied herein, by a balancing of bright field and dark field illumination. For example and without limitation, the point light source 154 can be moved to adjust the angle and distance between the point light source 154 and the syringe 152, and in this manner, contributions from bright and dark field illumination can be balanced.

Additionally or alternatively, a mixed mode can be achieved, for example and without limitation, by using an appropriately sized center beam blocker in a dark field system, to obtain a controlled combination of bright and dark view imaging. In a filled syringe, the contrast between silicone oil coating layer and drug solutions is low since silicone oil is transparent in the visible wavelength range. As such, when viewed by bright field imaging, it can be difficult to view the silicone oil coating. In contrast, in dark field imaging mode, where unscattered illumination light is removed from direct viewing by the camera or viewing eye, most or all of the image includes the optically discontinuous parts of an object which scatter or diffract light. As such, a pure dark field mode can be unable to include information from the optically continuous regions. Thus, for purpose of illustration and not limitation, and as embodied herein, the approaches described herein can be utilized to obtain a balance of bright field and dark field illumination, which can allow for more details of the silicone oil coating layer to be visible in the image.

The systems and methods described herein can thus achieve increased resolution, which can reveal additional details of the silicone oil layer morphology. The spatial resolution of an exemplary imaging system according to the disclosed subject matter can be near the optical diffraction limit, which can be about 20 microns or less, and as embodied herein, can be approximately 1 micron. As used herein, a lower number of microns indicates a higher resolution.

With continued reference to FIGS. 1A and 1B, at 106, an image is obtained of the resolved view. The image can be obtained, for example and not limitation, by an image detector such as a camera, and as embodied herein, the camera can be in optical communication with a lens. For purpose of illustration and not limitation, the system can thus include a lens 155, which as embodied herein, can be a 15× microscope objective lens (e.g., Thorlabs LMU 15× UVB). Lens 155 can be optically coupled to a camera 156, which as embodied herein can be a high resolution camera (e.g., Hamamatsu C4742-95). By adjusting the illumination, the resolution and contrast attained can allow for micron-sized features of the silicone oil layer to be resolved for analysis by a processor 157.

Figure 2A:
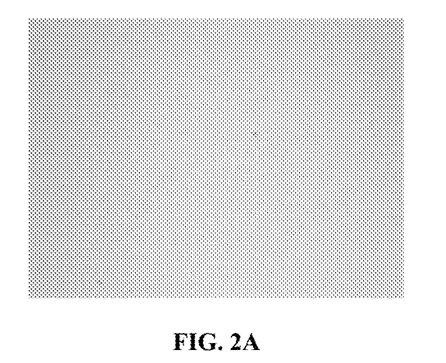
FIG. 2A is an exemplary bright field image for purpose of comparison with the disclosed subject matter.
Figure 2B:
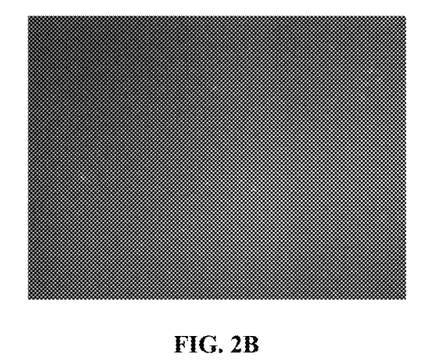
FIG. 2B is an exemplary dark field image for purpose of comparison with the disclosed subject matter.
Figure 2C:
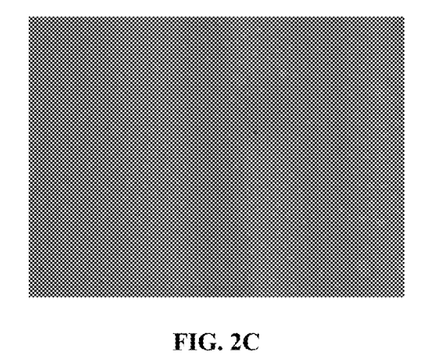
FIG. 2C is an exemplary image obtained in accordance with the disclosed subject matter.

For purpose of illustration and comparison, FIGS. 2A-2C were obtained under three different illumination modes, from the same area of a syringe filled with a model protein solution; the field of view is ≈0.7×0.7 mm. FIGS. 2A and 2B were obtained by conventional bright field and dark field illumination, respectively. No silicone oil beads can be definitively discerned in either image. For purpose of comparison and confirmation of the disclosed subject matter, using the system described herein, small silicone oil beads on the glass surface can be resolved (FIG. 2C), and in this manner, in operation, silicone oil beads as small as about 1 micron can be imaged on the glass surface of filled syringes.

Figure 3:
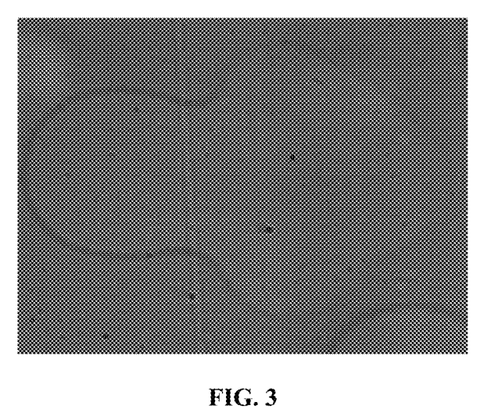
FIG. 3 is an exemplary image of a layer of substance on a portion of a surface of an empty syringe in accordance with the disclosed subject matter.

The systems and methods described herein can also be used to image syringes prior to filling, which, for purpose of illustration and not limitation, can be used to adjust and compare different silicone oil application procedures, and assess their effectiveness after filling. FIG. 3 was obtained from a siliconized empty syringe; field of view is ≈0.7×0.7 mm. As shown in FIG. 3, the distribution and surface coverage of silicone oil on its inner wall surface is visible and can be evaluated as described herein.

Referring again to FIGS. 1A and 1B, at 108, image data representing the image can be analyzed to generate a quantity representation between a lubricant and the container. The image can be analyzed by image processing software executed by processor 157. At 110, processor 157 can determine whether the container is acceptable based on the quantity representation. For example and not limitation, the interaction strength between the silicone oil layer and the glass surface in a syringe can be evaluated by analyzing high resolution images of the silicone oil layer. If the interaction is strong, the contact angle between silicone oil and glass surface can be small, as observed when silicone oil spreads out to form flat patches (as shown for example in FIG. 3). However, if the interaction is weak, the contact angle can be large, as exemplified by silicone oil spherical beads on the glass surface (as shown for example in FIG. 2C). A mixture of these two features can also be observed. As such, high resolution images can be utilized for quantitative interpretation of the lubrication features, and the ability to improve the effectiveness of siliconization procedures. Interpretation and scoring can be achieved by various image processing software. For example, machine learning based image analysis can be used for pattern recognition, and by training the software with "good" and "bad" images, a score can be assigned to a given syringe.

Figure 4A:
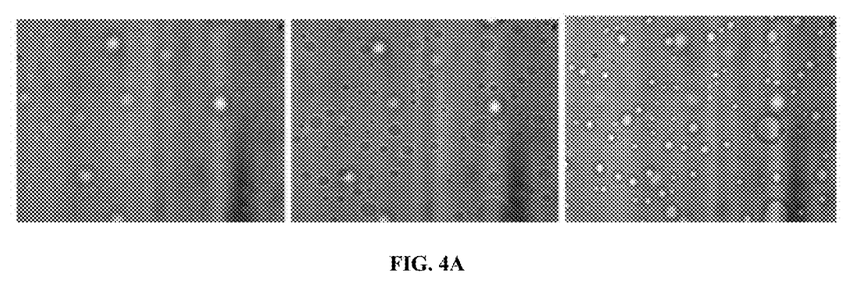
FIG. 4A is an exemplary series of images of a layer of substance on a portion of a surface of an empty syringe in accordance with the disclosed subject matter, each image of the series taken at a different level of focus.
Figure 4B:
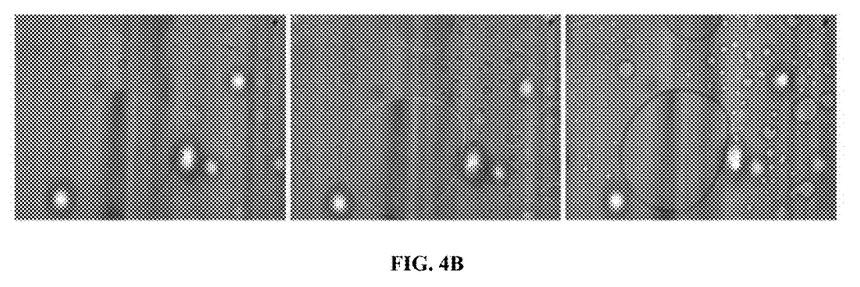
FIG. 4B is an exemplary series of images of a layer of substance on a portion of a surface of an empty syringe in accordance with the disclosed subject matter, each image of the series taken at a different level of focus.

Additional or alternative techniques can also be used to perform the image analysis. For example, and as embodied herein, due to the refractive index difference between silicone oil and drug solutions, silicone oil beads can have optical properties similar to small lenses on the glass surface. As such, when interaction between the silicone oil beads and the glass surface is weak (e.g., having a large contact angle) the beads can have optical properties similar to spherical lenses with short focal lengths, which can be sensitive to changes of focus in the high resolution imaging system. In contrast, when silicone oil interaction with the glass surface is strong (e.g., having a small contact angle and formation of patches), the patches can be inherently flat with long focal lengths, which can be less sensitive to changes in focus of the high resolution system. As such, by collecting images from the same area at several different focus levels, the interaction strength between silicone oil beads/patches and the glass surface of the syringe can be evaluated from a series of images (FIGS. 4A and 4B). This technique can be implemented, for example and without limitation, by programming an autofocusing lens, and/or by varying the distance between the imager and the syringe.

The morphology of silicone oil droplets (beads) can occur in a non-uniform configuration for a given syringe. For example, certain syringes can exhibit both strongly interacting silicone oil patches as well as weakly interacting beads. The latter can originate from silicone oil released from the wall into drug solution after filling of the syringe with the aqueous formulation. The resulting oil droplets can be coated with surfactant and/or other components (e.g., proteins) in the formulated solution, and if the droplets reattach to the glass surface, the resulting interaction with the glass surface can be very weak. Due at least in part to mild perturbations (e.g., shaking, or movement of the plunger) driving the weakly attached droplets back into solution, the droplets can be ineffective to contribute significantly to the lubrication properties in the syringe. As such, image analysis can be utilized for assessment and scoring of the effectiveness of the oil coating layer. Due at least in part to the size of the silicone oil beads or patches, which can vary from several hundred microns down to a few microns, the low resolution of certain instruments can be inadequate for characterizing the silicone oil layer. A high resolution image analysis can thus be used to determine characteristics of ill-behaved syringes.

Figure 5:
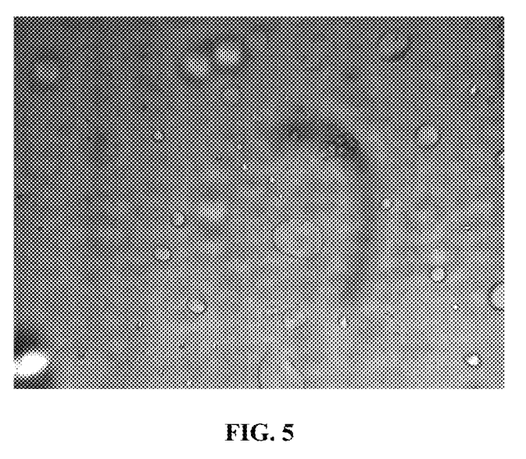
FIG. 5 is an exemplary image of a layer of substance on a portion of a surface of a prefilled syringe in accordance with the disclosed subject matter.

For purpose of illustration and not limitation, high resolution images of the silicone oil distribution before (e.g., FIG. 3) and after (e.g., FIG. 5) filling can be compared, and the coating can be shown to redistribute after filling. This redistribution can depend at least in part on the interaction strength between lubricant and glass surface, which as discussed above, can be modulated by components in the formulation and conditions stemming from siliconization, handling, and storage procedures. As such, characterizing empty syringes alone can be less accurate to evaluate the injection performance compared to characterizing filled syringes.

Figure 6A:
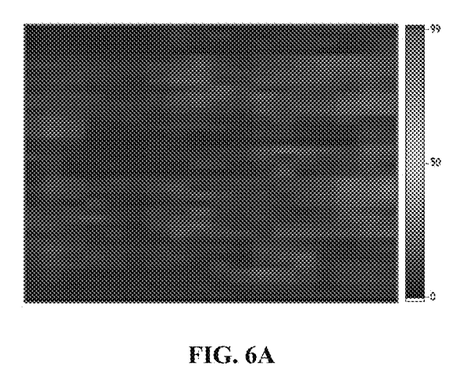
FIG. 6A is a diagram illustrating analysis of exemplary syringes using a conventional system for purpose of comparison with the disclosed subject matter.
Figure 6B:
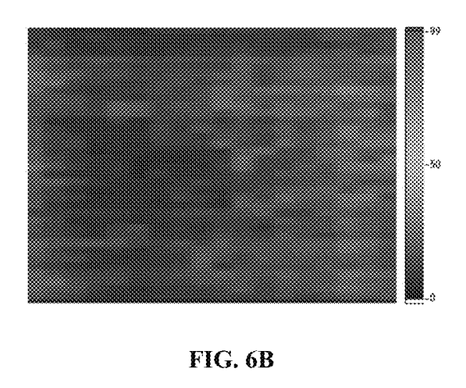
FIG. 6B is a diagram illustrating analysis of exemplary syringes using a conventional system for purpose of comparison with the disclosed subject matter.

For purpose of illustration and comparison with the disclosed subject matter, using a model protein solution, the ZebraSCI system was configured to analyze 10 ill-behaved syringes and 10 well-behaved syringes. The ZebraSCI results are shown in FIGS. 6A and 6B, respectively (color bars represent the surface coverage of silicone oil).

Figure 7A:
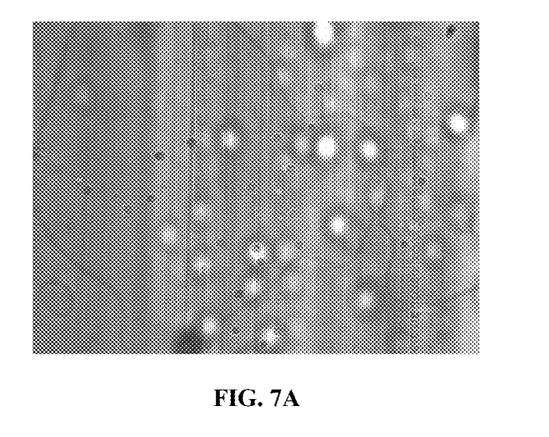
FIG. 7A is an exemplary image of a layer of substance on a portion of a surface of a prefilled syringe determined to be suitable in accordance with the disclosed subject matter.
Figure 7B:
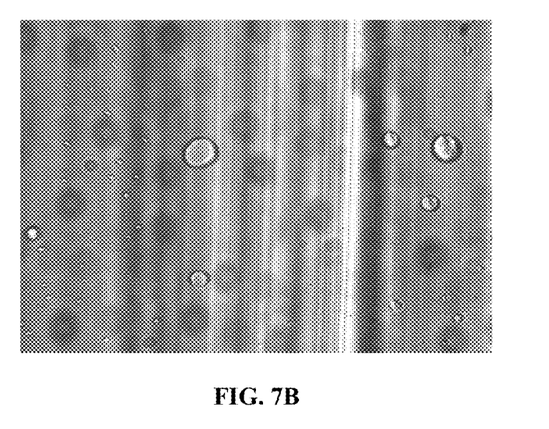
FIG. 7B is an exemplary image of a layer of substance on a portion of a surface of a prefilled syringe determined to be unsuitable in accordance with the disclosed subject matter.

The ZebraSCI analyses detected no meaningful differences in the quality of interaction of lubricant on the syringe between the two groups. These 20 syringes were also evaluated by RapID before filling and again no differences between the two groups were discernible. In contrast, analysis using the imager according to the disclosed subject matter showed that the well-behaved syringes contain a preponderance of strongly interacting silicone oil patches (FIG. 7A), while the morphology of the oil layer in the ill-behaved syringes is dominated by loosely attached silicone oil beads (FIG. 7B).

The systems and methods according to the disclosed subject matter can be automated, which can allow for high throughput screening of empty and filled syringes. During testing, several images of the same region of the syringe can be recorded in less than one second. By translating and rotating the syringe, multiple positions can be evaluated for silicone oil distribution and morphology.

In operation, the systems and techniques described herein can be implemented in a manufacturing environment for manufacturing syringes or for manufacturing a drug product contained in a prefilled syringe. For purpose of illustration and not limitation, with reference to FIG. 1B, processor 157 can determine a container is suitable or unsuitable, as described herein, and can initiate a command to an automated manufacturing system to, for example and without limitation, reject an unsuitable container, provide an indication that a container is suitable or unsuitable, physically sort unsuitable containers from suitable containers, and/or load a new container for testing.

Processor 157 can perform the techniques described herein by executing software embodied in one or more tangible, computer-readable media, such as a memory unit. The memory unit can read the software from one or more other computer-readable media, such as a mass storage device or from one or more other sources via a communication interface. The software can cause the processor 157 to execute the particular analysis or response process or particular processes including defining data structures stored in the memory unit and modifying such data structures according to the processes defined by the software. Processor 157 can receive data from one or more input devices, for example and as embodied herein, the detection device including camera 156. Processor 157 can communicate with an output interface, such as a display to allow the processor to provide an indication to a user whether a container is of an acceptable quality, and/or to an automatic manufacturing system to perform packaging, rejecting, or sorting of containers based on the analysis. Additionally or alternatively, processor 157 can communicate with light source 154 to adjust the position and/or orientation of the light source 154 relative to the container 152 as described herein.

The foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

We claim:

1. A method for inspecting a distribution and a morphology of a lubricant in a container, comprising:
   selectively illuminating at least a portion of a surface of the container using a light source;
   adjusting the light source to create a resolved view of the lubricant with sufficient contrast to show a layer of the lubricant disposed on the surface of the container;
   obtaining an image of the resolved view of the illuminated portion of the surface of the container using an image detector;
   analyzing image data representing the image of the resolved view, using a data processor, to generate a quantity representing a quality of interaction between the lubricant and the surface of the container; and
   determining whether the container is acceptable based upon the quantity generated.

2. The method of claim 1, wherein the lubricant comprises a silicone oil.

3. The method of claim 1, wherein the container comprises a pre-filled syringe.

4. The method of claim 1, wherein the light source comprises a point light source or collimated light.

5. The method of claim 1, wherein adjusting the light source comprises adjusting the light source to illuminate the illuminated portion using a combination of bright-field illumination and dark-field illumination.

6. The method of claim 1, wherein adjusting the light source comprises adjusting at least one of an angle and a distance of the light source relative to the container to control a balance of contributions from bright field and dark field illumination of a sample to be collected by the detector, thereby creating the resolved view with sufficient contrast to show the layer of the lubricant disposed on the surface of the container.

7. The method of claim 1, wherein adjusting the light source comprises modifying a size of a center beam blocker of a conventional dark field microscope.

8. The method of claim 7, wherein adjusting the light source further comprises selecting the size of the center beam blocker to allow a contribution from bright field imaging to create the resolved view with sufficient contrast to show the layer of the lubricant disposed on the surface of the container.

9. The method of claim 1, wherein the image detector comprises a digital microscope.

10. The method of claim 9, wherein the digital microscope has a resolution of about 20 microns or less.

11. The method of claim 1, wherein analyzing the image data comprises recognizing patterns and morphologies of illuminated regions of the lubricant.

12. The method of claim 11, wherein analyzing the image data further comprises comparing the recognized patterns and morphologies to a set of known image data, each known image data of the set of known image data having a known quantity representing a known quality of interaction between a sample lubricant and a sample container.

13. The method of claim 12, wherein analyzing the image data further comprises assigning a score to the container based on the comparison of the recognized patterns and morphologies to the set of known image data.

14. The method of claim 1, further comprising obtaining a plurality of images of the resolved view of the illuminated portion of the surface of the container.

15. The method of claim 14, further comprising changing a focal distance of the image detector for each of the plurality of images of the resolved view.

16. The method of claim 15, wherein analyzing the image data comprises determining whether an area of illuminated regions of the lubricant has a substantially constant size or intensity in each of the plurality of images of the resolved view.

17. The method of claim 1, further comprising identifying regions of strongly and weakly bound lubricant, and rejecting the container if the quantity is below a predetermined threshold.

18. The method of claim 1, wherein the inspection is performed on a plurality of containers in a high-throughput manner.

19. The method of claim 1, further comprising providing an indication of whether the container has been determined to be acceptable based upon the quantity generated.

20. A system for inspecting a distribution and a morphology of a lubricant in a container, comprising:
   a light source configured to selectively illuminate at least a portion of a surface of the container, the light source adapted to be adjusted to create a resolved view of the lubricant with sufficient contrast to show a layer of the lubricant disposed on the surface of the container;
   an image detector configured to obtain an image of the resolved view of the illuminated portion of the surface of the container; and
   a data processor coupled to the image detector and configured to:
   analyze image data representing the image of the resolved view to generate a quantity representing a quality of interaction between the lubricant and the surface of the container, and
   determine whether the container is acceptable based upon the quantity generated.

* * * * *